(12) United States Patent
Falk

(10) Patent No.: US 6,181,416 B1
(45) Date of Patent: Jan. 30, 2001

(54) SCHLIEREN METHOD FOR IMAGING SEMICONDUCTOR DEVICE PROPERTIES

(75) Inventor: Robert Aaron Falk, Renton, WA (US)

(73) Assignee: OptoMetrix, Inc., Renton, WA (US)

(*) Notice: Under 35 U.S.C. 154(b), the term of this patent shall be extended for 0 days.

(21) Appl. No.: 09/292,101

(22) Filed: Apr. 14, 1999

Related U.S. Application Data

(60) Provisional application No. 60/081,713, filed on Apr. 14, 1998.

(51) Int. Cl.$^7$ ............................................. G01N 21/41
(52) U.S. Cl. .................................. 356/129; 324/753
(58) Field of Search .................... 356/128, 129, 356/30; 324/752, 753

(56) References Cited

U.S. PATENT DOCUMENTS

| | | | |
|---|---|---|---|
| 3,468,610 | * 9/1969 | Muffoletto | 356/129 |
| 3,934,199 | * 1/1976 | Channin | 324/753 |
| 4,188,123 | * 2/1980 | Kleinknecht | 356/128 |
| 5,754,298 | 5/1998 | Falk . | |
| 5,850,255 | 12/1998 | Falk . | |

OTHER PUBLICATIONS

Dixon, W.P. "Radial schlieren for detecting small index gradients", Applied Optics, vol. 21, No. 11 (Jun. 1, 1982) p. 1896.*

L.A. Vasil'ev, *Schlieren Methods*, Israel Program for Scientific Translations, pp. 69–81, 96–113, 170–197, 204–205, 242–253, 1971.

H.K. Heinrich et al., "Noninvasive sheet charge density probe for integrated silicon devices", *Appl. Phys. Lett.48*: 1066–1068, 1986.

M. Goldstein et al., "Heterodyn interferometer for the detection of electric and thermal signals in integrated circuits through the substrate", *Rev. Sci. Instrum. 64*:3009–3013, 1993.

R.A. Falk et al., "Electro–Optic Imagery of High–Voltage GaAs Photoconductive Switches", *IEEE Trans. Electron Devices 42*: 43–9, 1995.

J.C. Adams, et al., "Electro–Optic Imagery of Internal Fields in (111) GaAs Photoconductors", *IEEE Trans. Electron Devices 42*: 1081–5, 1995.

* cited by examiner

*Primary Examiner*—Richard A. Rosenberger
(74) *Attorney, Agent, or Firm*—Black Lowe & Graham PLLC

(57) ABSTRACT

An optical beam (3) passes through an illuminator (18), a semiconductor device (70), and an imager (20) to form a test object image (17) on a camera (16). Intensity variations in the object image (17) correspond to carrier density and temperature gradients inside the semiconductor device (70).

22 Claims, 6 Drawing Sheets

SCHLIEREN METHOD FOR IMAGING SEMICONDUCTOR DEVICE PROPERTIES

This application claims benefit to U.S. Provision application Ser. No. 60/081,713 filed Apr. 14, 1998.

FIELD OF THE INVENTION

This invention relates to methods and apparatus for imaging the carrier density and temperature of semiconductor circuits.

BACKGROUND OF THE INVENTION

Schlieren Imagery

Schlieren imagery is an imaging process whereby changes in the angular deviation of an optical beam are transformed into changes in the intensity of the Schlieren image. A Schlieren imaging apparatus contains two image planes, a source image plane, where an image of the optical source is produced, and an object image plane, where an image of the object illuminated by the optical source is produced. Refractive index gradients in the object produce angular deviations in the optical beam. These angular deviations are transformed by the Schlieren optics into deviations in the position of the optical source image. A filter, e.g. a knife-edge, placed in the plane of the source image causes the angular deviations to produce intensity shifts in the object image.

There are many variations in the basic Schlieren concept. For example, dark field microscopy is a form of Schlieren imagery. However, all Schlieren apparatus utilize a finite size source with some preset geometry and a mask (typically at the source image plane) which causes amplitude variations to appear in the object image as a result of refractive index gradients in the object. For the following discussion, a knife-edge type Schlieren system as described in *Schlieren Methods*, L. A. Vasil'ev, pages 86–149 is assumed. For small angular deviations, it can be shown that the change in object image intensity is linearly related to the refractive index gradient in the illuminated object by $$\Delta I = kI_0 \int \frac{\partial n}{\partial x} dz, \quad (1)$$

where k is a constant relating to the source size, object transmission and reflection parameters, and focal powers of the imaging system, $I_0$ is the illumination intensity, n is the refractive index of the object, z is in the propagation direction of the optical beam, and x is the direction perpendicular to the knife-edge and z.

Semiconductor Imagery

The refractive index of semiconductors is known to be affected by the internal properties of the semiconductor. Specifically, the electric field, temperature, and carrier density will all cause changes in the refractive index. Table 1 contains theoretical estimates for the magnitude of these effects in terms of small signal variations for GaAs (gallium arsenide). The effects of electric field, E, temperature, T, and electron density, $N_e$, on refractive index, n, are shown. The effect of hole density is similar to electron density. Other semiconductor materials, such as silicon will show similar behaviors.

TABLE 1

| Semiconductor Property | Refractive Index |
|---|---|
| Electric Field | $\frac{\delta n}{\delta E} = 3 \times 10^{-9} (cm/V)$ |
| Temperature | $\frac{\delta n}{\delta T} = 3 \times 10^{-4} (1/K)$ |
| Carrier Density | $\frac{\delta n}{\delta N_c} = 4 \times 10^{-21} (cm^3)$ |

Electric fields only affect the refractive index of semiconductors which are noncentrosymmetric. For example strong electro-optic effects occur in GaAs but not in silicon. Techniques for obtaining electro-optic images in noncentrosymmetric semiconductors, specifically GaAs are described in "Electro-Optic Imagery of High-Voltage GaAs Photoconductive Switches," R. A Falk, J. C. Adams, C. D. Capps, S. G. Ferrier, and J. A Krinsky, IEEE Trans. Electron Devices 42, 43–9 (1995), and "Electro-Optic Imaging of Internal Fields in (111) GaAs Photoconductors," J. C. Adams, R. A. Falk, S. G. Ferrier, and C. D. Capps, IEEE Trans. Elect. Devices 42, 1081–85, (1995). These techniques involve analyzing the polarization rotation of light passing through the GaAs sample, whose wavelength is well below the absorption bandedge. In order to compensate for the multivalued nature of the polarization rotation, specialized algorithms were utilized to process the images. Although a remarkable measurement, the techniques employed will not work in semiconductors such as silicon and are only useful for electric fields, i.e. they are not applicable to temperature or carrier density measurements.

Heinrich et al. and Goldstein et al. have demonstrated optical, high-speed sampling of carrier density and thermal effects in semiconductors at a single spatial point. Electric field could be sensed indirectly through the change in carrier density, which occurs in the depletion region of reversed biased junctions. The work of the first group is described in "Noninvasive Sheet Charge Density Probe for Integrated Silicon Devices," H. K. Heinrich, D. M. Bloom, and B. R Hemenway, Appl. Phys. Lett. 48, 1066–8, (1986). The work of the second group is described in "Heterodyne Interferometer for the Detection of Electric and Thermal Signals in Integrated Circuits through the Substrate," M Goldstein, G. Solkner, and E. Gornik, Rev. Sci. Instrum. 64, 3009–13 (1993). Both of those optical arrangements utilized interferometric means to extract a signal from the changes in refractive index caused by the two effects. In both cases, a pair of optical beams is brought in through the backside of the semiconductor device. One beam, used as a reference, is reflected off of a convenient point on the upper surface of the device and brought back into the optical detector. The second beam is positioned onto the point of interest, reflected off of the upper surface and combined with the reference beam to form the interferometric signal. In the case of Heinrich, et al., a modified Nomarski interference microscope was utilized as the interferometric system. Goldstein, et al. utilized a variant on a heterodyne, interference microscope.

The detection schemes of Heinrich, et al. and Goldstein, et al. were performed at a single point. An extension of their work could be to scan the optical beam(s) in order to assemble an image of the target. An imaging system may one-day be devised that utilizes a point-by-point sequential scanning method in which an image of an entire object may be created by accumulating several images of different optical spots on the object. While effective for some circumstances, there are, however, situations in which sequential scanning may still be impractical. Specifically, the timing of the scanning should preferably correspond to the timing of changes in the refractive index of the object. If, for example, a "single shot" event occurs in which the refractive index change only occurs for a small, fixed period of time, then the optical spot may not be present at the point of the refractive index change when it occurs. In that case, the image obtained would not properly reflect the change in the refractive index.

An adequate solution to the above problems has eluded those skilled in the art. More specifically, a need exists for a method or apparatus for imaging the internal characteristics of a semiconductor circuit, including temperature and carrier density, independent of the timing of the circuit.

SUMMARY OF THE INVENTION

In accordance with this invention, a method and apparatus for imaging the carrier density and temperature in a semiconductor circuit or device is provided. An imaging system in accordance to this invention includes an optical source combined with a first knife-edge. The optical beam from this combination is collimated and passed through a semiconductor device. An image of the combination is then formed at the position of a second knife edge. In addition, an image of the semiconductor device is formed at some distance behind the second knife-edge. The arrangement of the optical system is such that angular deviations in the optical beam caused by refractive index gradients in the semiconductor device are transformed into intensity variations in the image of the semiconductor device. The refractive index gradients result from carrier density or temperature variations inside the semiconductor device. Thus, an image of the carrier density or temperature gradients in the semiconductor device is obtained.

In addition to the optical system described above, the invention includes means to place the semiconductor device into a desired state and to obtain an image of the device carrier density or temperature during the time period that it is in said state. Alternatively, a sequence of temporal images can be obtained as the device state evolves.

DETAILED DESCRIPTION OF THE INVENTION

Figure 1:
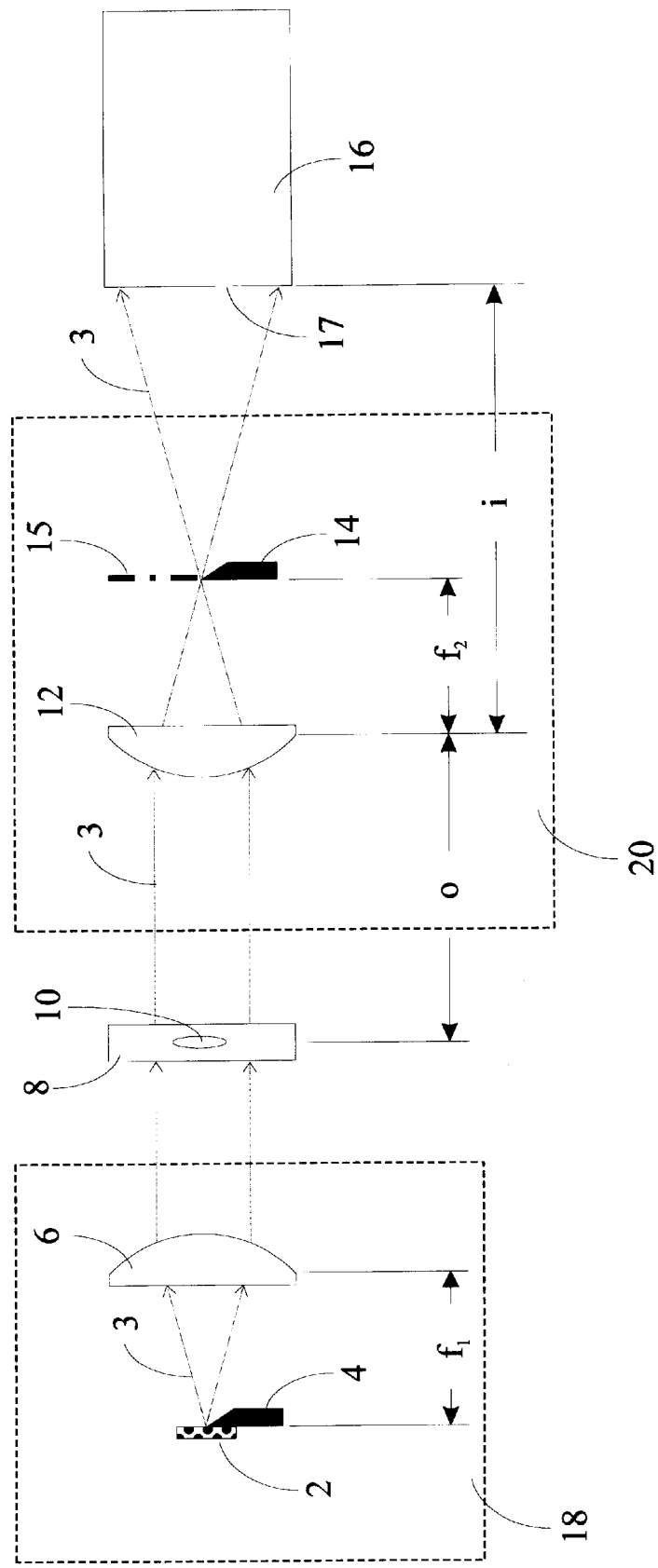
FIG. 1 is a schematic view of a first transmission arrangement for a Schlieren imaging system.

FIG. 1 sets forth one embodiment of a Schlieren imaging system for imaging refractive index variations in a test object, specifically as applied to imaging refractive index changes which occur in semiconductor devices due to temperature and carrier density.

The imaging system includes an optical source 2, which creates an optical beam 3. The optical beam 3 shown in FIG. 1 represents those rays emanating from a point on the optical source 2 and is indicative of the total set of rays from the entire optical source. A portion of the optical source 2 is obscured by a knife-edge 4 located proximate to the optical source 2. The optical source 2 and the knife-edge 4 are separated by a distance $f_1$ from the first lens 6, where $f_1$ is the focal length of the first lens 6. The optical beam 3 is thereby collimated by the first lens 6. The group of objects composed of the optical source 2, the knife-edge 4, and the first lens 6 make up an illuminator 18 for the Schlieren imaging system.

The optical beam 3 exiting the illuminator 18 passes through a test object 8, which contains a refractive index gradient 10. For a test object 8, such as a semiconductor device, the refractive index gradient 10 may result from temperature or carrier density gradients within the semiconductor device. It is an important aspect of this embodiment that the wavelength of the optical beam 3 be selected so that it lies in a spectral region for which the test object 8 is transparent. For example, assuming the test object 8 is a semiconductor device, generally, semiconductors have a bandedge. Wavelengths shorter than the bandedge are highly absorbed, and wavelengths longer than the bandedge pass through with little absorption. For silicon and GaAs, the bandedge is in the near infrared region of the spectrum.

The portion of the optical beam 3 that passes through the refractive index gradient 10 sustains a change in direction with respect to the portion of the optical beam 3 that does not pass through the refractive index gradient 10. The degree of angular change in direction is in direct proportion to the magnitude of the refractive index gradient 10 at the point that the optical beam 3 passes through said refractive index gradient 10.

The modified optical beam 3 then passes through a second lens 12 and continues on to a second knife-edge 14. The group of objects composed of the second lens 12 and the second knife-edge 14 make up an imager 20 for the Schlieren imaging system.

Figure 2:
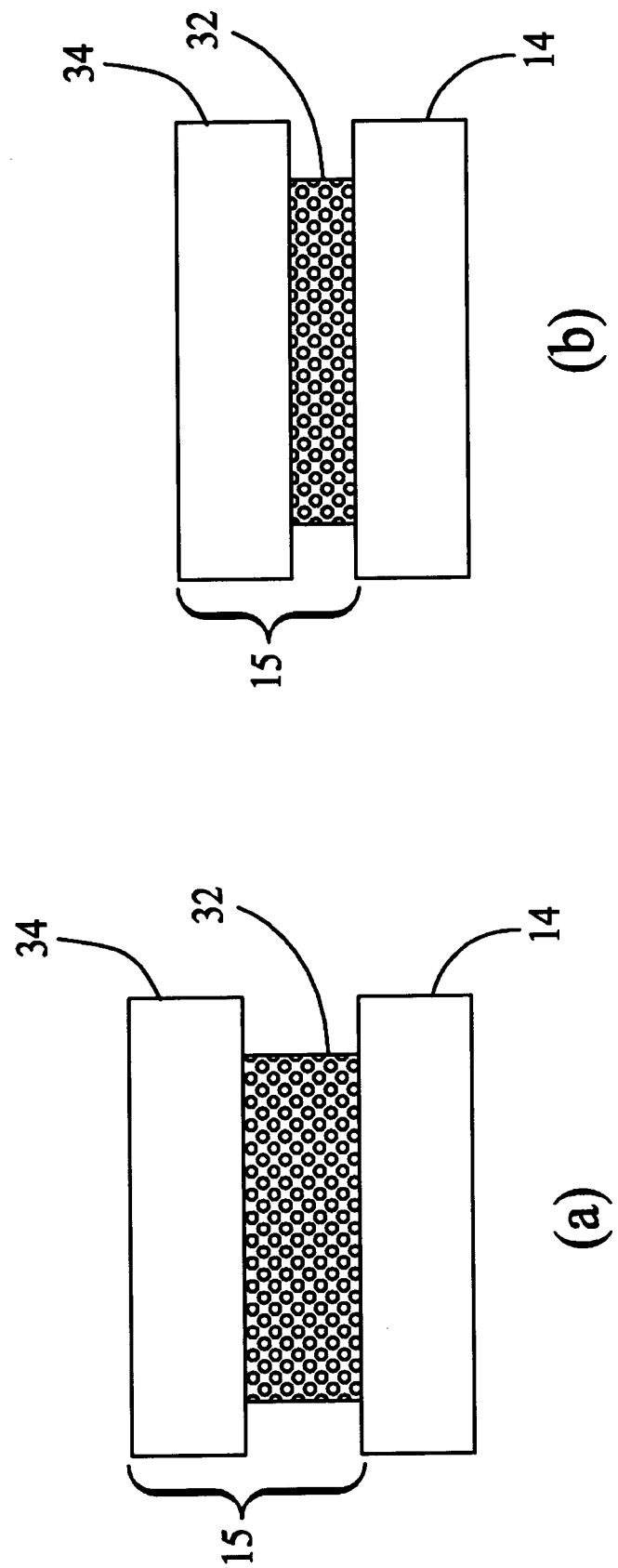
FIG. 2 demonstrates the change in the image position of the source and first knife edge with respect to the second knife edge in a Schlieren imaging system as the refractive index gradient in the test object is changed.

The second lens 12 and the second knife-edge 14 are separated by a distance $f_2$, where $f_2$ is the focal length of the second lens 12. A source image 15 of the combination of the optical source 2 and the first knife-edge 4 is thereby formed at the position of the second knife-edge 14. FIG. 2 shows details of the plane transverse to the optical beam 3 in which the image 15 is formed. The source image 15 in FIG. 1 is composed of the combination of an optical source image 32, which is the image of the optical source 2, and a first knife-edge image 34, which is the image of the first knife-edge 4, as shown in FIG. 2. The optical source image 32 and the first knife-edge image 34 appear inverted vertically with respect to the source 2 and the first knife-edge 4. The vertical position of the source image 15 with respect to the vertical position of the second knife-edge 14 modulates the amount of energy in the optical beam 3. FIGS. 2 (a) and (b) show two positions of the source image 15 with position (a) allowing more optical energy to pass than position (b).

Referring back to FIG. 1, a further affect of the second lens 12 is to transform angular changes produced by the refractive index gradient 10 into position changes in the image 15. In this fashion, the amount of optical energy passing the second knife edge is directly proportional to the vertical angular deviation caused by the refractive index gradient 10. Each point in the test object 8 produces a related source image 15. Thus, the vertical angular deviations caused by the refractive index gradient 10 changes the optical energy passing through each point in the test object 8 in an amount proportional to the refractive index gradient 10 at that point. Placement of the test object 8 at a distance, o, in front of the second lens 12 produces a test object image 17 of the test object 8 at a distance, i, behind the second lens 12. The test object image 17 can be detected by a camera 16 placed at that position. Due to the Schlieren processes described above, the intensity at each point in the test object image 17 will be changed by an amount proportional to the refractive index gradient 10 at the corresponding point in the test object 8.

Figure 3:
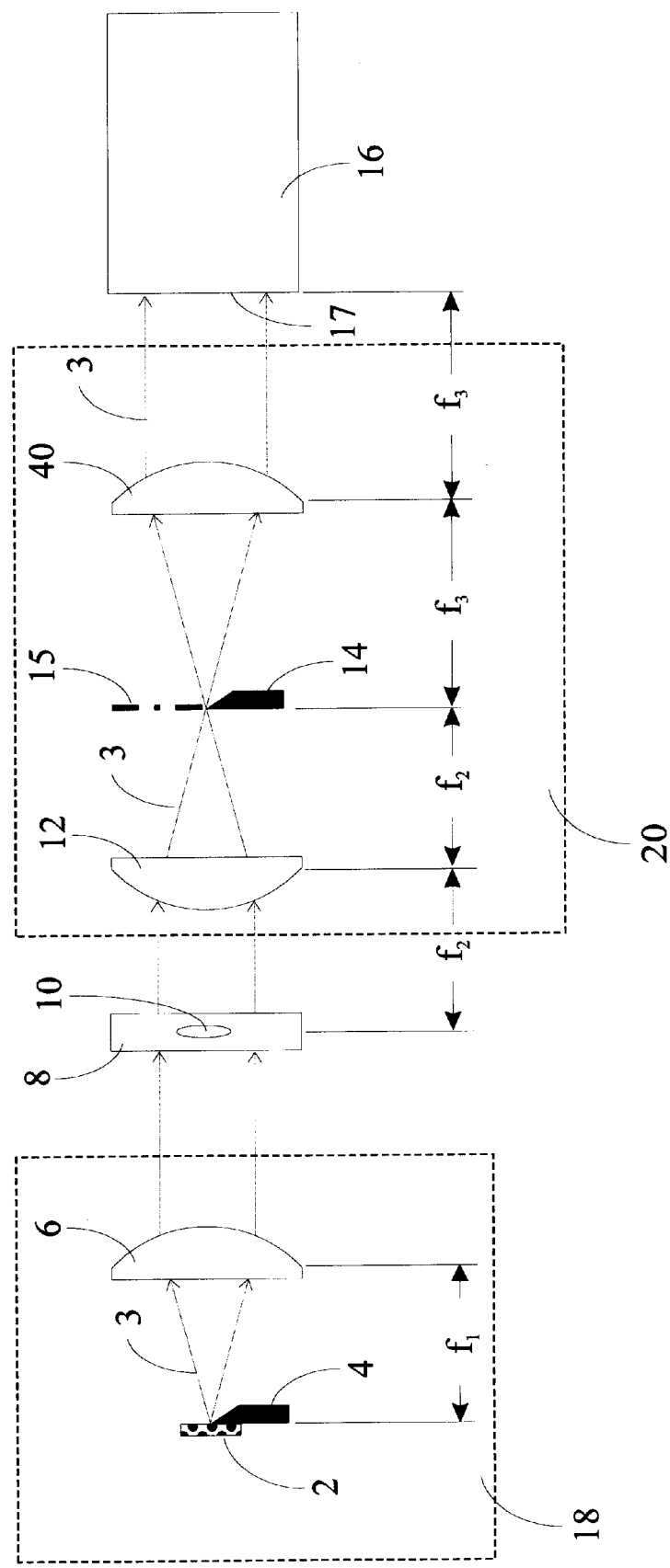
FIG. 3 is a schematic view of a second transmission arrangement for a Schlieren imaging system.

FIG. 3 sets forth a second embodiment of a Schlieren imaging system for imaging refractive index variations in a test object. The operation of the embodiment shown in FIG. 3 is similar to the operation of the embodiment shown in FIG. 1, except that a third lens 40 is added to the second embodiment of the Schlieren imaging system. The addition of the third lens 40 allows a separation of the two functions of the second lens 12 in the first embodiment. Specifically, in FIG. 3 the second lens 12 produces the source image 15 and the third lens 40 produces the test object image 17. Separation of these two functions allows each lens to be independently optimized for each specific function. In addition, this two-lens arrangement reduces second order focussing effects caused by the refractive index gradient 10. Best operation occurs when the test object 8 is placed at a distance $f_2$ in front of the second lens 12, the second knife edge is placed at a distance $f_2$ behind the second lens 12 and a distance $f_3$ in front of the third lens 40, which produces the test object image 17 at a distance $f_3$ behind the third lens 40, where $f_2$ is the focal length of the second lens 12 and $f_3$ is the focal length of the third lens 40. The imager 20 in this second embodiment also contains the third lens 40 in addition to those items contained in the imager 20 for the first embodiment. The function of the imager 20, however, is otherwise identical.

Figure 4:
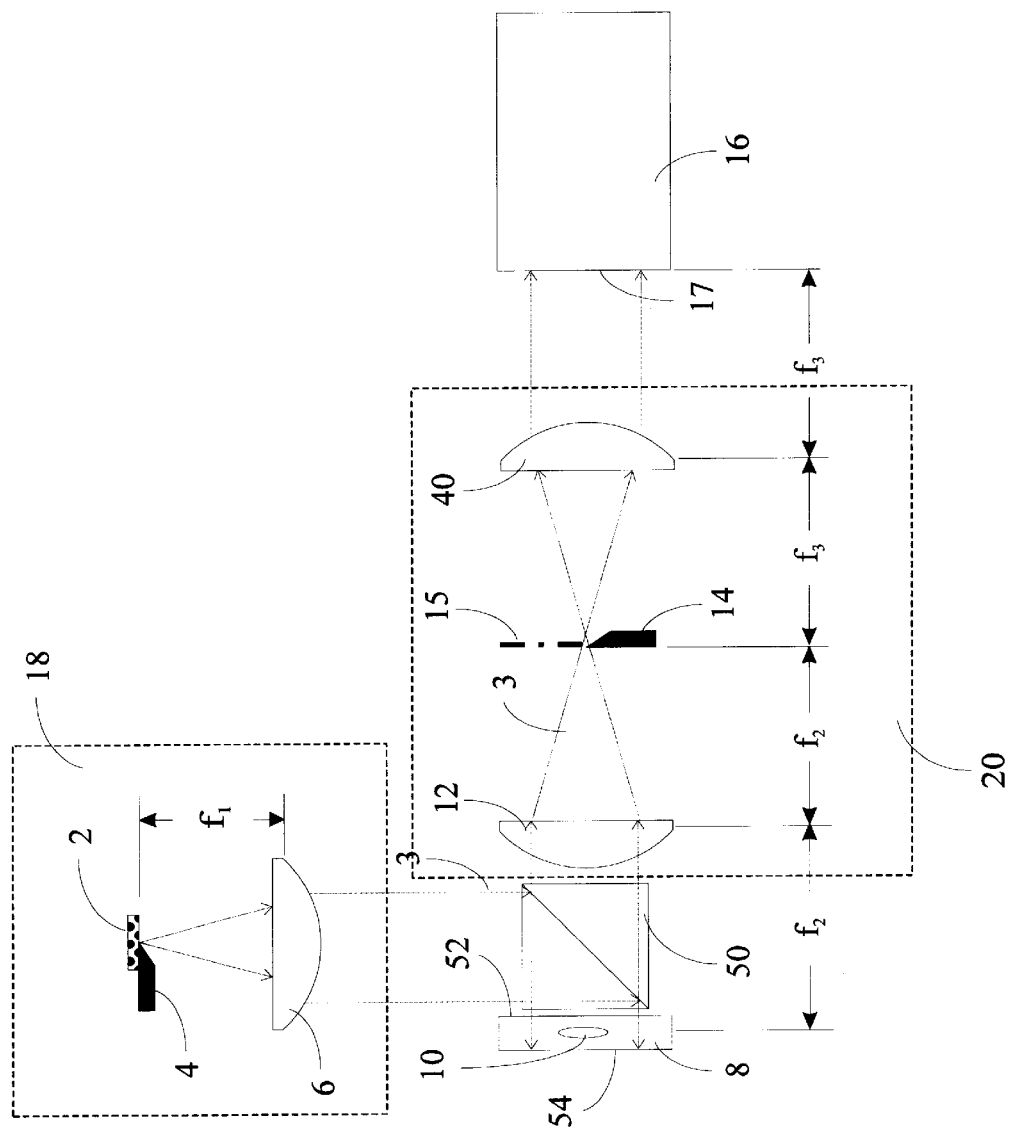
FIG. 4 is a schematic view of a reflection arrangement for a Schlieren imaging system.

FIG. 4 sets forth a third embodiment of a Schlieren imaging system for imaging refractive index variations in a test object. The operation remains substantially as described for the first and second embodiments; however, the test object 8 is now a reflective object instead of a transmissive object. A beam splitter 50 is added to the optical system to allow the optical beam 3 to be directed from the illuminator 18 towards the test object 8. The optical beam 3 passes through a bottom surface 52 of the test object 8 and is reflected by a top surface 54 back through the test object 3 towards the beam splitter 50. The beam splitter 50 allows light reflected from the test object 8 to pass through to the imager 20. In the case of the test object 8 being a semiconductor device, reflection occurs at the top surface 54 due to metal layers, dielectric layers, and the semiconductor-to-air dielectric interface. The bottom surface 52 is typically polished to an optical finish and can be optionally anti-reflection coated to allow the optical beam to pass with minimal losses and aberrations.

From the forgoing discussion it is clear that Schlieren imaging systems can be realized in a wide variety of embodiments. In addition to the above embodiments, Schlieren imaging systems are envisioned that utilize mirrors in place of lenses or utilize specially shaped masks in place of knife-edges. The embodiments described above are merely illustrative of the Schlieren imaging techniques which can be utilized to image refractive index gradients in semiconductor devices.

Figure 5:
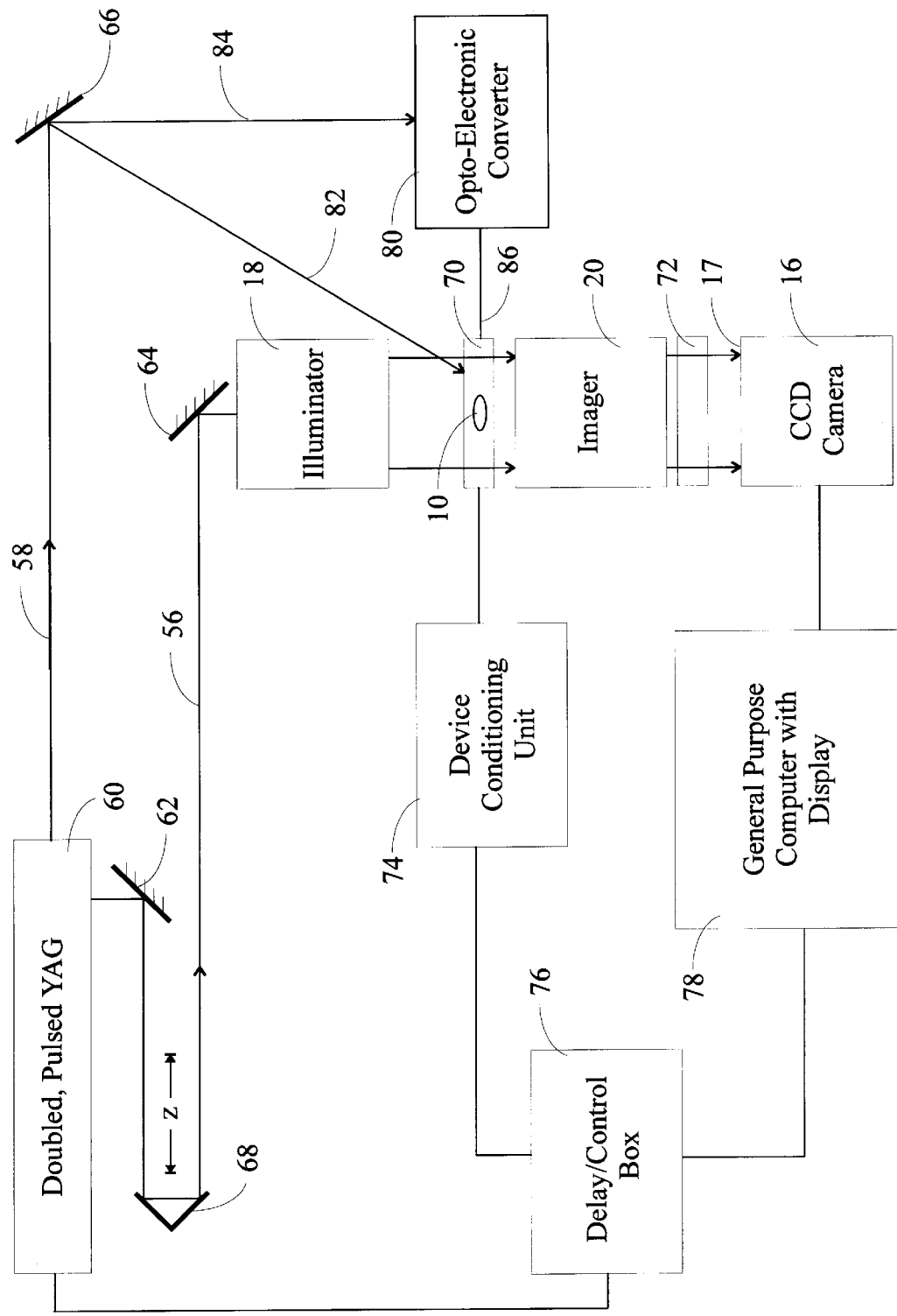
FIG. 5 is a schematic view of a first method for utilizing a Schlieren imaging system to image the carrier density and temperature in a semiconductor device.

FIG. 5 shows in schematic form yet another embodiment of an imaging system for imaging the internal characteristics of carrier density and temperature inside a semiconductor device 70. At the heart of the apparatus is a Schlieren imaging system composed of the illuminator 18, the imager 20, and the camera 16. However, the optical source 2 described above is replaced by a laser 60, which produces a first optical beam 56 used as the input to the illuminator 18, and a second optical beam 58 to trigger a semiconductor device 70. The semiconductor device 70 replaces the test object 8 in the previous embodiments of the Schlieren imaging system.

The laser 60 may, for example, be a pulsed, doubled YAG laser, which produces short optical pulses at a fundamental wavelength of 1064 nanometers and a doubled wavelength of 532 nanometers. In this example, the first optical beam 56 corresponds to the fundamental wavelength and the second optical beam 58 corresponds to the doubled wavelength. The first optical beam 56 is reflected by a first turning mirror 62, a retro-reflective delay 68, and a second turning mirror 64. The second turning mirror 64 directs the first optical beam 56 so that it passes through the illuminator 18, the semiconductor device 70, the imager 20, and a blocking filter 72. The first optical beam 56 is finally detected by the camera 16. As described above, the test object image 17 detected by the camera 16 will contain intensity variations in proportion to any refractive index gradients 10 contained within the semiconductor device 70.

The blocking filter 72 is optional, but may be advantageous when luminescence from the semiconductor device 70 is deleterious to the quality of the test object image 17. Generally, luminescence in a semiconductor will occur in a narrow wavelength band centered near the bandedge wavelength. The blocking filter 72 is designed to pass the wavelength of the first optical beam 56 while blocking any luminescence that occurs in the semiconductor device 70. As described above, transparency of the semiconductor device 70 to the first optical beam 56 requires that the wavelength of said beam be longer than the bandedge wavelength. The blocking filter 72 can be a narrow band transmission filter centered around the wavelength of the first optical beam 56, or an edge filter with the edge lying between the bandedge wavelength and the wavelength of the first optical beam 56.

The second optical beam 58 is directed towards the semiconductor device 70 or an opto-electronic converter 80 by a third turning mirror 66. The second optical beam 58 is used to trigger the semiconductor device 70, with triggering events corresponding to pulses in the second optical beam 58. Triggering of the semiconductor device 70 may occur directly due to photoconductive effects in the semiconductor device 70. In this case the second optical beam 58 directly illuminates the semiconductor device 70 as illustrated by a first ray 82. For example, if the semiconductor device 70 is a photoconductive switch made of GaAs, then the bandedge wavelength is approximately 820 nanometers. Since the wavelength, 1064 nanometers, of the first optical beam 56 is below the bandedge wavelength for GaAs, the first optical beam 56 passes through the semiconductor device 70 with little absorption. However, the wavelength, 532 nanometers, of the second optical beam 58 is above the bandedge wavelength and, therefore, the second optical beam 58 is absorbed by the semiconductor device 70. The absorption of the second optical beam 56 initiates photoconduction in the semiconductor device 70, which changes the carrier density and temperature within the semiconductor device 70, creating the refractive index gradient 10.

Alternatively, the second optical beam 58 can be used to activate or control the opto-electronic converter 80. The second optical beam 58 is directed towards the opto-electronic converter 80 as illustrated by a second ray 84. The opto-electronic converter 80 converts the second optical beam 58 into an electronic trigger signal 86, which is utilized to trigger the semiconductor device 70 and create the refractive index gradient 10 by electronic processes. The opto-electronic converter 80 can be implemented by a number of well-known means.

Static, Continuous Wave ("CW") operation of the Schlieren optical system is possible. However, the more general case involves temporal variations in the refractive index gradient 10. Specifically, the semiconductor device 70 will generally be an operational circuit, which is changing its state with time. For example, the semiconductor device 70 could be a GaAs photoconductive switch in the process of closing. Triggering, as described above, allows the semiconductor device 70 to be placed into a known condition at a known point in time. Pulses in the first optical beam 56 and the second optical beam 58 are fully synchronized when derived from a laser 60, such as a pulsed double YAG. The relative timing between pulses in the two beams can therefor be adjusted through use of a retro-reflective delay 68. The retro-reflective delay 68 returns the first optical beam 56 directly back along its path with a small transverse displacement. Moving the retro-reflective delay along the path, z, of the first optical beam 56 produces a change in the total path length of the first optical beam 56. Thus, the relative delay between pulses in the first optical beam 56 and the second optical beam 58 can be adjusted. In this fashion, the semiconductor device 70 can be set to a known operational state at the time the pulse from the first optical beam 56 passes through said device and the test object image 17 will represent a time slice of the operational state of the semiconductor device 70. Stepping the position of the retro-reflective delay 68 allows a sequence of test object images 17 to be obtained, which display the time evolution of the refractive index gradient 10, with time steps corresponding to delay steps. Note that each test object image 17 is obtained in one step, a process not possible with the existing point-by-point scanning imaging system.

While not essential to the invention, a general-purpose computer 78 may be added to the components of the embodiment shown in FIG. 5 to capture and display the test object image 17 recorded by the camera 16. In addition, the general-purpose computer 78 can perform any desirable post processing of the test object image 17. Additionally, a device conditioning unit 74 may be used in conjunction with the semiconductor device 70. The device conditioning unit 74 may perform a function as simple as supplying electrical power to the semiconductor device 70 or as complex as supplying digital test vectors. For the more complex cases, coordination of the timing of the laser 60, the device conditioning unit 74 and the general purpose computer 78 may be desirable. A delay/control box 76 may then be used to supply this coordination. As an example, the general purpose computer 78 supplies a signal to the delay box 76 indicating that the camera 16 is ready to capture the test object image 17. This signal is sent by the delay/control box 76 to the device conditioning unit 74, which produces the correct state of the semiconductor device 70. The delay/control box 76 then sends a delayed signal to the laser 60, which in response produces a pulse in both the first optical beam 56 and the second optical beam 58. Several alternative delay and control options will be apparent to those skilled in the art.

Figure 6:
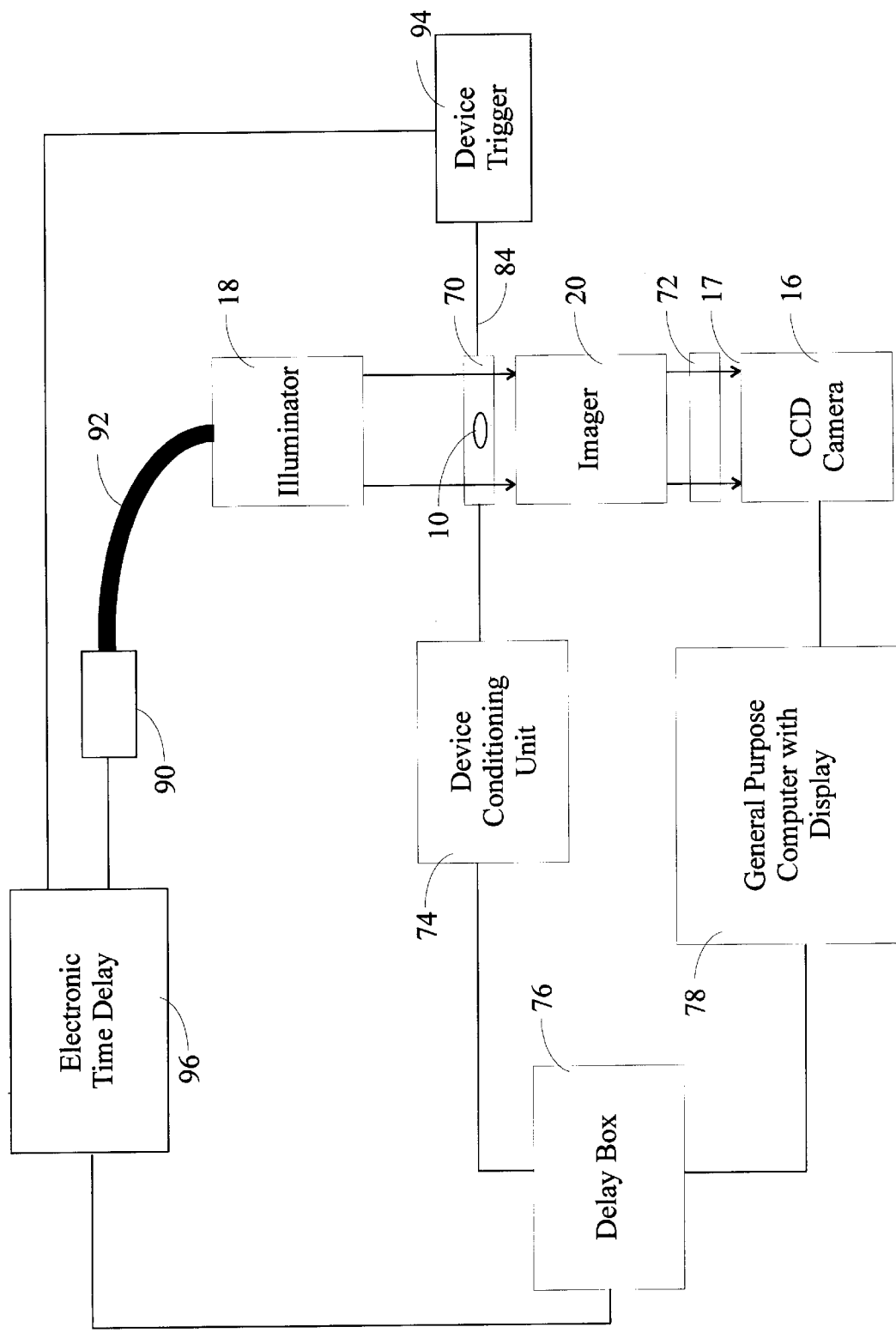
FIG. 6 is a schematic view of a second method for utilizing a Schlieren imaging system to image the carrier density and temperature in a semiconductor device.

FIG. 6 is still another embodiment of an imaging system for imaging the internal characteristics of carrier density and temperature inside a semiconductor device 70. This embodiment shares much in common with the embodiment illustrated in FIG. 5 and may produce substantially the same results. The differences, seen in FIG. 6, begin with the substitution of an opto-electronic source 90 for the laser 60. The opto-electronic source 90 can be any optical source which can be modulated electronically, such as a laser diode, a light emitting diode, or a CW laser used in conjunction with an external modulator. The optoelectronic source 90 is coupled to the illuminator 18 via an optical fiber 92. The operation of the remainder of the optical path from the illuminator 18 to the camera 16 remains substantially identical to the embodiment shown in FIG. 5.

Timing for this embodiment of the imaging system is obtained via an electronic time delay 96 and a device trigger 94. The electronic delay 96 performs substantially the same function as the retro-reflective delay 68, but without requiring mechanical movement. A device trigger 94 performs the same function as the optoelectronic converter 80, except that the input to the device trigger 94 is electronic instead of optical. Further, the electronic delay 96 drives the opto-electronic source 90 to produce an optical pulse at the desired delay with respect to the state of the semiconductor device 70 as described above. Those skilled in the art will be aware of several practical implementations for the electronic delay 96.

While the preferred embodiments of the invention have been illustrated and described, it will be apparent that various changes can be made therein without departing from the spirit and scope of the invention.

The embodiments of the invention in which an exclusive property or privilege is claimed are defined as follows:

1. A method for imaging an internal characteristic of a semiconductor circuit device, comprising:
   a) Generating an optical beam with an illuminator, the optical beam having a wavelength selected such that the semiconductor circuit device passes the optical beam without undo absorption;
   b) Radiating the optical beam toward an imager, the semiconductor circuit device being disposed between the illuminator and the imager such that the optical beam passes through the semiconductor circuit device and the internal characteristic of the semiconductor circuit device imposes an angular deviation in the optical beam arriving at the imager, the imager operative to focus the optical beam into an image of the illuminator and another image of the semiconductor circuit device; and
   c) Detecting an intensity variation in the image of the semiconductor circuit device, the intensity variation being related to the angular deviation imposed on the optical beam by the internal characteristic of the semiconductor circuit device.

2. The imaging method of claim 1, further comprising:
   setting the semiconductor circuit device, having a present state, to a state different than the present state; and
   wherein radiating is delayed a specific amount of time with respect to setting the semiconductor circuit device to the different state.

3. The method of claim 2, wherein at least one of the present state and the different state are operational states for the semiconductor circuit device.

4. The imaging method of claim 1, wherein the internal characteristic of the semiconductor circuit device is a refractive index gradient.

5. The imaging method of claim 4, wherein the refractive index gradient is related to a variation in the temperature of the semiconductor circuit device.

6. The imaging method of claim 4, wherein the refractive index gradient is related to a variation in the carrier density of the semiconductor circuit device.

7. An apparatus for imaging the internal temperature and carrier density in a semiconductor circuit device, comprising:
   a) an imaging system comprising an illuminator for generating an optical beam, an imager for focusing the optical beam, and an image detector for detecting images formed by the optical beam;
   b) the optical beam passing from the illuminator to the imager and having a wavelength selected such that the semiconductor circuit device passes the optical beam without undo absorption while allowing for detection of the optical beam by the image detector, and
   c) the semiconductor circuit device located between the illuminator and the imager in the path of the optical beam such that the changes in the internal temperature and carrier density of the semiconductor circuit device impose a change in the intensity of the optical beam arriving at the image detector.

8. The apparatus of claim 7, further including a trigger controlled by the imaging system and operative to set the state of the semiconductor circuit device at a specific time interval with respect to the time at which the optical beam passes through the semiconductor circuit device.

9. The apparatus of claim 8, wherein the trigger is a second optical beam focused on the semiconductor circuit device and that directly sets the state of the semiconductor circuit device.

10. The apparatus of claim 8, wherein the trigger is a second optical beam focused on an opto-electric converter that electronically sets the stat of the semiconductor circuit device in response to the second optical beam.

11. The apparatus of claim 8, further comprising means to adjust the specific time interval between setting the state of the semiconductor circuit device and the time at which the optical beam passes through the semiconductor circuit device.

12. The apparatus of claim 11, wherein the means to adjust the specific time interval is a retro-reflector displaced along the optical axis of the optical beam.

13. The apparatus of claim 8, wherein the illuminator is under the control of a controller and the trigger is under the control of the controller, the controller being operative to adjust the relative timing of the illuminator and the trigger.

14. The method of claim 8, wherein the state of the semiconductor circuit device is an operational state.

15. An apparatus for detecting characteristic of a semiconductor circuit device, the characteristic having a refractive index gradient, the apparatus comprising:
   an illuminator, including an optical source and a first lens, the optical source capable of radiating an optical beam to the first lens, the first lens being positioned a distance from the optical source roughly equal to the focal length of the first lens, the first lens being further configured to collimate the optical beam for transmission along an optical beam path;
   an imager positioned along the optical beam path, the imager including a second lens configured to focus the optical beam to a focal point; and
   an image detector positioned at a distance along the optical beam path and beyond the focal point of the second lens, the image detector being capable of detecting intensity variations in the optical beam;
   wherein if the semiconductor circuit device is placed between the illuminator and the imager along the optical beam path, angular deviations in the optical beam caused by the refractive index gradient are transformed into intensity variations in the optical beam and are detected by the image detector.

16. The apparatus of claim 15, wherein the refractive index gradient is a result of a spatial variation of the carrier density of the semiconductor circuit device.

17. The apparatus of claim 15, wherein the refractive index gradient is a result of a temporal variation of the carrier density of the semiconductor circuit device.

18. The apparatus of claim 15, wherein the refractive index gradient is a result of a spatial variation of the temperature of the semiconductor circuit device.

19. The apparatus of claim 15, wherein the refractive index gradient is a result of a temporal variation of the temperature of the semiconductor circuit device.

20. The apparatus of claim 15, wherein the imager further includes a filter positioned at the focal point of the second lens to modulate the amount of energy in the optical beam.

21. The apparatus of claim 15, wherein the illuminator comprises a laser.

22. The apparatus of claim 21, wherein the image detector is a camera.

* * * * *